United States Patent [19]

Warriner

[11] Patent Number: Plant 6,664

[45] Date of Patent: Mar. 14, 1989

[54] ROSE PLANT JACGLOW

[75] Inventor: William A. Warriner, Tustin, Calif.

[73] Assignee: Jackson & Perkins Company, Medford, Oreg.

[21] Appl. No.: 81,434

[22] Filed: Aug. 3, 1987

[51] Int. Cl.[4] ..... A01H 5/00

[52] U.S. Cl. ..... Plt./18

[58] Field of Search ..... Plt./18

*Primary Examiner*—James R. Feyrer

*Attorney, Agent, or Firm*—Majestic, Gallagher, Parsons & Siebert

[57] ABSTRACT

A rose variety of the hybrid tea class is provided having high centered, Red Group 49 blooms that heavily produced on long cutting stems, leathery, dark green foliage and resistance to powdery mildew.

1 Drawing Sheet

SUMMARY OF THE INVENTION

The present invention relates to a new and distinct variety of rose plant of the hybrid tea class, which was originated by me by crossing the variety White Masterpiece, U.S. Plant Pat. No. 2,998, with the variety Futura, U.S. Plant Pat. No. 3,569.

The primary objective of this breeding was to produce a new rose variety of the hybrid tea class combining a classical form with high flower production. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Delicate pink flower color;
2. Long stems;
3. Resistance to powdery mildew;
4. Peduncles that include both glands and prickles;
5. Leathery, dark green foliage;
6. Heavy flower production.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacglow". Color terminology is in accordance with The Royal Horticultural Society Colour Chart except where an ordinary dictionary significance for the color is apparent.

Observations of the buds and flowers were made from specimens grown in a garden at Irvine, Calif. in the Summer.

Flower

The blooming habit is continuous. The bud size is one and one-half inches when the petals start to unfurl. The bud form is long, pointed ovoid. The bud color when sepals first divide is near Red Group 49D; when half blown, the upper side of petals is near Red Group 49D, with a greater color intensity in the center (near Red Group 49C), and the lower side of petals is near Red Group 49D. The sepals have a color near Green Group 138B. The surface texture is covered in fine hairs. There are three appendaged sepals normally appendaged, and two unappendaged sepals with hairy edge. The receptacle color is near Green Group 138B with a funnel shape, medium size and hairy surface. The peduncle is medium, and has a prickly and glandular surface. Peduncle color is medium green and the peduncle is stiff, erect and heavy.

Bloom

Bloom size is large, with an average open size of four and one-half inches, borne singly or several together. The stems are strong and long. The form when first open is high center. The petals then flatten and the outer petals curl back and quill. Under normal conditions there are thirty-five to forty petals. The upper side of petals is near Red Group 49C to 49D, and the reverse side of the petals is near Red Group 49C. The base of petals has a small yellow half-moon (near Yellow Group 3B) at the point of attachment to the peduncle with the major color being near Red Group 49D. There are no variegations. The general tonality at the end of the first day shows no change in color. At the end of the third day, there remains no discoloration.

The fragrance is slight to moderate. The petal texture is thick, of a round to deltoid shape, and the form is flat with tips slightly recurved and outer petals moderately quilled.

The arrangement is imbricated with few, small petaloids in the center. The blooms hang on and dry, and last on the plant for a long period and as a cut flower for a long time.

Reproductive Parts

The anthers are large and many, of yellow color, arranged regularly around the styles and are mixed with a few petaloids. The filaments are reddish, the pollen is gold yellow, the styles are reddish, and the stigmas are greenish white.

Plant

A vigorous, upright growth of bush form.

Foliage

Medium size, normal in quantity. The new foliage is bronze colored that turns dark green as old foliage. Normal mid-stem leaves have five leaflets.

The leaflets are of an oval pointed shape, are leathery, and have a serrated edge. The serration is single and small in size. Petiole rachis is reddish, and petiole underside is rough with prickles. Stipules are long and the edges are glandular. The foliage is resistant to mildew under normal growing conditions at Irvine, Calif.

Wood

New wood is reddish, with a smooth bark. Old wood is green with a smooth bark.

Prickles

There are an ordinary number of prickles on main canes from the base and on laterals from the main canes. The form is medium and hooked downward. Color when young is red.

Parentage

The seed parent was the variety White Masterpiece, U.S. Plant Pat. No. 2,998. The pollen parent was the variety Futura, U.S. Plant Pat. No. 3,569.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by light pink, high centered blooms, heavy flower production on long stems, leathery, dark green foliage, resistance to powdery mildew, and peduncles including glands and prickles.

* * * * *

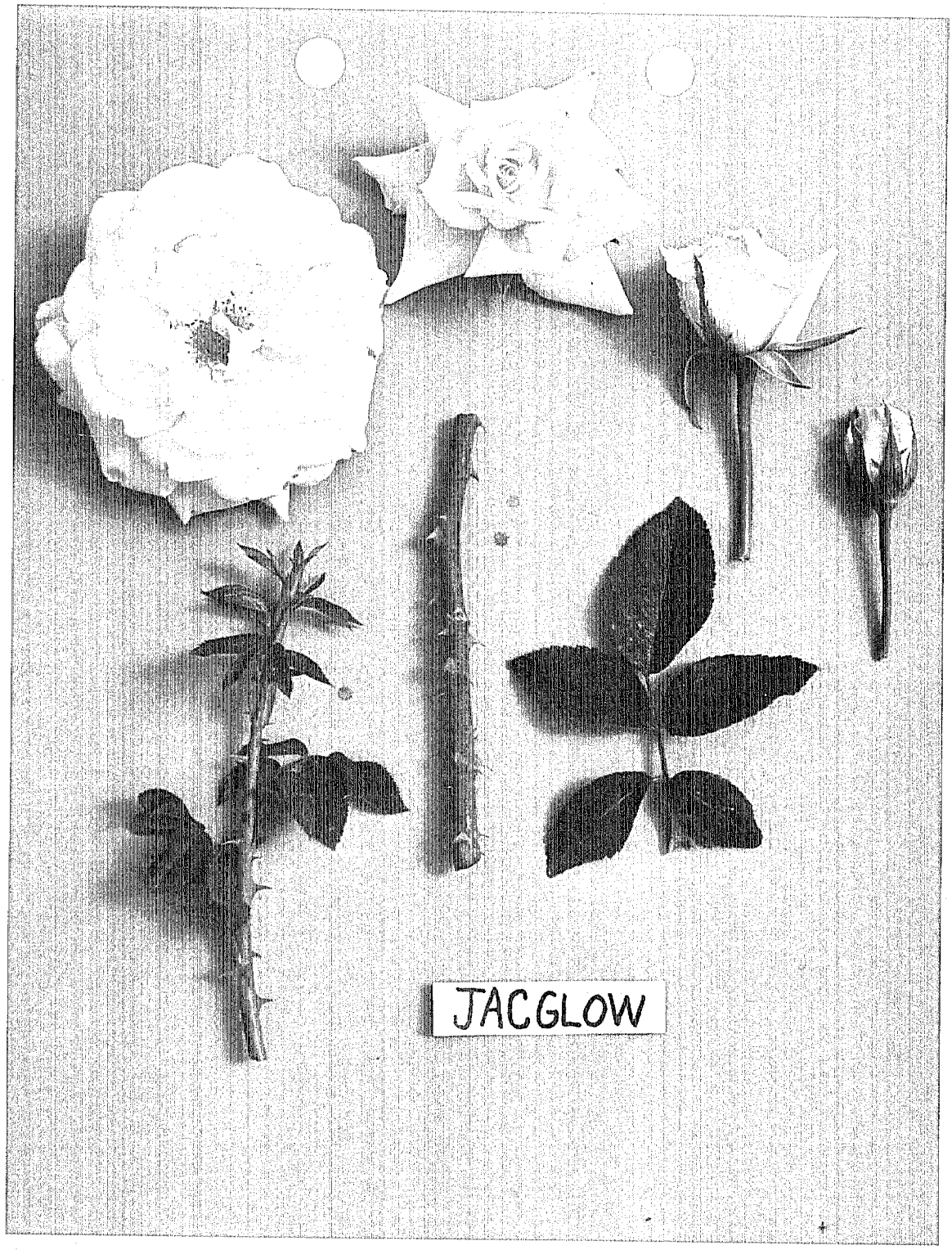
JACGLOW